United States Patent [19]
Baumgartner et al.

[11] 3,937,759
[45] Feb. 10, 1976

[54] HYDROGENATION PROCESS

[75] Inventors: Herman J. Baumgartner, Cypress; Jaroslav G. Balas, Palos Verdes Penn., both of Calif.

[73] Assignee: Shell Oil Company, Houston, Tex.

[22] Filed: May 1, 1974

[21] Appl. No.: 465,771

[52] U.S. Cl. .......... 260/879; 260/85.1; 260/94.7 H; 260/96 HY; 260/880 B; 260/677 H
[51] Int. Cl.² ......................................... C08C 19/02
[58] Field of Search............. 260/94.7 H, 85.1, 879, 260/880 B; 450/613

[56] References Cited
UNITED STATES PATENTS

| | | |
|---|---|---|
| 3,673,281 | 6/1972 | Bronstert et al. ............... 260/880 B |
| 3,700,748 | 10/1972 | Winkler .............................. 260/879 |
| 3,792,127 | 2/1975 | Gillies ........................... 260/880 B |

*Primary Examiner*—William F. Hamrock

[57] ABSTRACT

The process of hydrogenating olefin compounds utilizing certain hydrogenation catalysts can be interrupted or halted by the addition to the reaction mixture of an organometallic reducing agent. Hydrogenation can be resumed by subsequent addition of an alcohol or other compound capable of reacting with the reducing agent.

10 Claims, 1 Drawing Figure

HYDROGENATION REACTION CONTROL OF ISOPRENE-STYRENE COPOLYMER (80°C, 700 PSIG, 18% SOLIDS, 4.0 MMOLES Ni/LB POLYMER Al/Ni = 2.5 MOLAR)

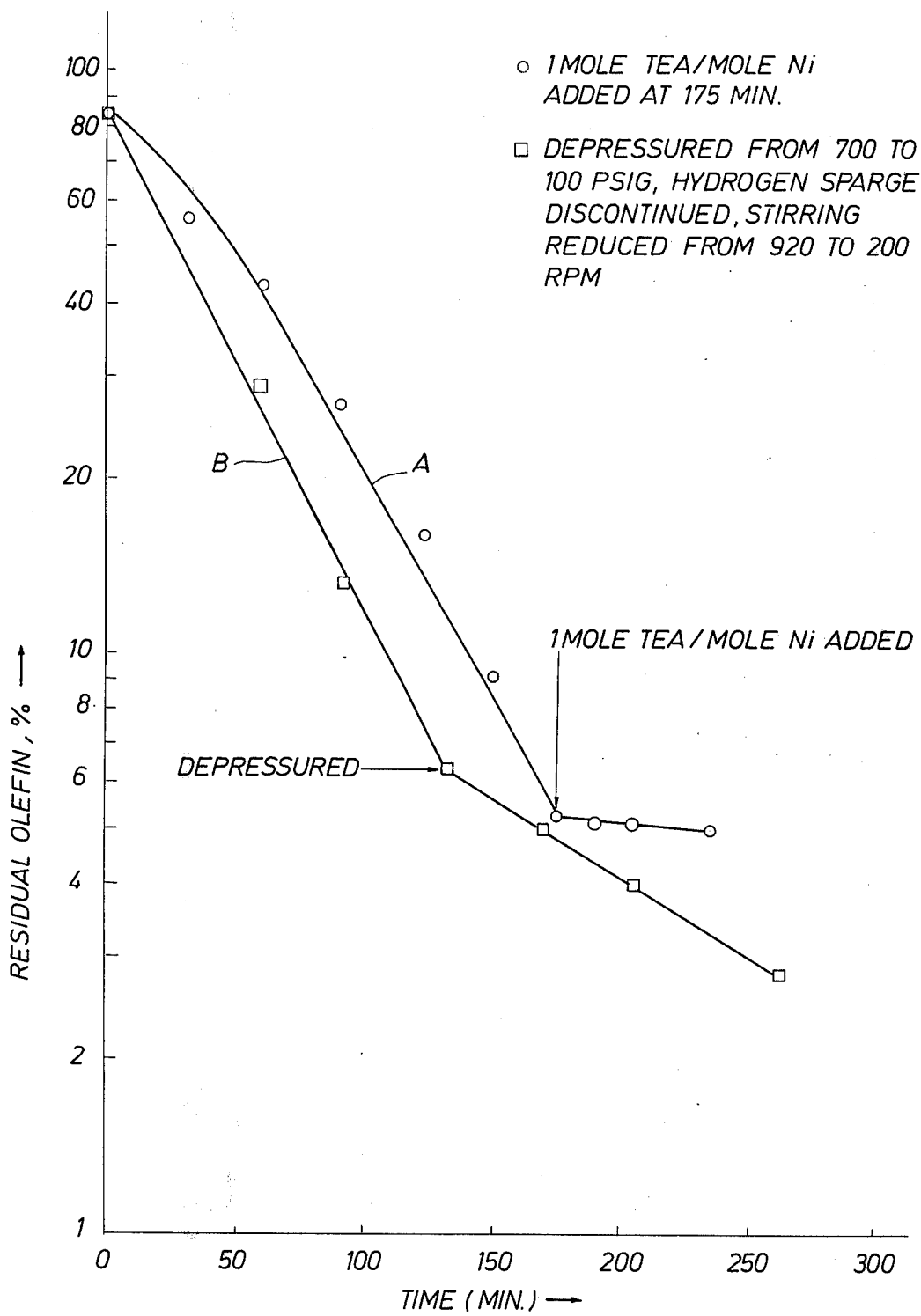
FIG. 1 HYDROGENATION REACTION CONTROL OF ISOPRENE-STYRENE COPOLYMER (80°C, 700 PSIG, 18% SOLIDS, 4.0 MMOLES Ni/LB. POLYMER Al/Ni = 2.5 MOLAR)

HYDROGENATION PROCESS

BACKGROUND OF THE INVENTION

Hydrogenation of unsaturated compounds has been investigated in many aspects, particularly with respect to the catalysts employed. For example, U.S. Pat. No. 3,130,237, suggests hydrogenating unsaturated compounds by the use of certain cobalt complexes. U.S. Pat. No. 3,205,218 teaches hydrogenation of olefinic compounds utilizing a complex of a nickel or cobalt compound with certain aluminum reactants. U.S. Pat. No. 3,113,986 is related and suggests hydrogenation in the presence of the reaction products of certain metal alkoxides with aluminum trialkyls. Finally, U.S. Pat. No. 3,595,942 teaches selective hydrogenation of block copolymers with reaction products of aluminum trialkyls and metal alkoxides or carboxylates. In all of these catalyst systems, a ratio of organometallic reducing agent to carboxylate can be found which provides optimum hydrogenation activity. Other organometallic reducing agents also can be used, such as alkyl lithiums.

While the hydrogenation processes taught by the above patents are useful for reducing unsaturation, no means is provided for interrupting the hydrogenation with the capability of resuming hydrogenation if the latter is desired. Several important reasons exist for the desirability of a controlled interruption of this kind. For example, in a number of instances, it is desired to hydrogenate a stated percentage of the double bonds of the compound being hydrogenated. However, there is no direct means for ascertaining during the hydrogenation the extent of reduction which has been achieved. Consequently, it is necessary to rely upon experience for stopping the hydrogenation and recovering the product. This, of course, is an undesirable procedure especially where a given degree or level of hydrogenation may be critical to the quality or eventual end use of the reduced product. On the other hand, if the hydrogenation is stopped such as by the addition of water or the like or introduction of air, then it is virtually impossible to renew hydrogenation without injection of a completely new quantity of hydrogenation catalyst. This is undesirable. Another situation in which interruption is desirable is in the hydrogenation of unsaturated copolymeric compounds wherein it is desirable to reduce one type of double bond without materially affecting a second type of double bond in the same molecule. Thus, it is highly desirable to achieve a process which may be interrupted at will, permit removal of samples of the reaction mixture for testing of residual unsaturation or any other desirable property and at the same time to be able to resume hydrogenation if this is subsequently desirable.

OBJECTS OF THE INVENTION

It is an object of the present invention to provide an improved hydrogenation process. It is a further object of the invention to provide a controlled hydrogenation process which may be interrupted and then resumed at will. Other objects will become apparent during the following detailed description of the invention.

STATEMENT OF THE INVENTION

Now, in accordance with the present invention, an improved hydrogenation process is provided wherein olefinically unsaturated hydrocarbons are hydrogenated in the presence of an active hydrogenation catalyst comprising the reaction product of a organometallic reducing agent and an alkoxide or carboxylate of a metal of the group consisting of cobalt, nickel or iron used at ratios selected for hydrogenaton activity and after a hydrogenation period, reversibly interrupting the hydrogenation by injection of a supplementary amount of organometallic reducing agent. Still in accordance with this invention, it has been found that hydrogenation may be resumed in the above interrupted system by addition thereto of an alcohol, organic acid or other suitable proton doning agent or a supplementary proportion of cobalt, nickel or iron carboxylate or alkoxide in an amount sufficient to react with the previously added supplementary organometallic reducing agent.

The unsaturated organic compounds which may be treated according to the invention may be monomeric or polymeric. Any hydrocarbon containing aliphatic unsaturation, that is, ethylenic or acetylenic unsaturation, may be reduced by the process of this invention. Exemplary of these aliphatically unsaturated hydrocarbons that may be hydrogenated are olefins and cycloolefins, such as butene-1, butene-2, 2-methylbutene-2, 2,3-dimethylbutene-2, amylene, hexene-1, hexene-2, 2-methylpentene-1,2-methylhexene-2, heptene-1, heptene-2, octene, dodecene, cyclohexene, methylcyclohexene, vinylcyclohexane, styrene, alpha-methylstyrene, etc., and acetylenic hydrocarbons, such as acetylene, propyne, butyne, ethynylbenzene, etc., and polyunsaturated hydrocarbons such as allenes dienes, polyenes, diynes, etc., such as allene, isoprene, vinylcyclohexene, etc., and mixtures of any of these unsaturated hydrocarbons. The process of this invention is accordingly of considerable importance in the hydrogenation of gasoline fractions, etc. It is also useful for the selective hydrogenation of feedstocks containing aliphatically and aromatically unsaturated hydrocarbons since only the aliphatic unsaturation is hydrogenated. Unsaturated hydrocarbon rubbers, as for example, natural rubber, polyisoprene, etc., can be hydrogenated, partially or completely, if desired, whereby they are made more resistant to attack by ozone.

More particularly, the block copolymers especially contemplated comprise at least one polymer block of a monoalkenylarene and at least one polymer block of a conjugated diene. Suitable block copolymers are the following:

polystyrene-polybutadiene
polystyrene-polyisoprene
polystyrene-polyisoprene-polystyrene
polystyrene-polybutadiene-polystyrene.

Homologs and analogs are contemplated as well, including especially block copolymers in which the monoalkenylarene may be not only styrene, but also higher homologs such as alpha-methylstyrene or tertiary butylstyrene. The conjugated dienes contemplated would normally be butadiene or isoprene as illustrated above, but may include other dienes such as piperylene or the like. Mixtures of these monomers may be present in each of the polymer blocks if so desired. The hydrogenation process also relates closely to the hydrogenation of tapered or random copolymers especially those involving monomers such as those listed above.

The hydrogenation catalyst especially contemplated comprises the reaction products of organometallic reducing agents (e.g. aluminum trihydrocarbyls or alkyl lithiums) with carboxylates or alkoxides of a metal of the group consisting of cobalt, nickel or iron, as well as mixtures thereof. Normally, the molar ratio of organometallic reducing agent to the metal carboxylate or alkoxide will be between 0.1:1 to 10:1 preferably between about 0.5:1 to 6:1 to obtain a catalyst with optimum activity. The hydrocarbyl substituents of the organometallic reducing agents preferably comprise those having from 2 to 10 carbon atoms, each including an alkyl radical such as ethyl, propyl, butyl, pentyl, hexyl, octyl, decyl and dodecyl. The metal carboxylates may comprise particularly salts of fatty acids preferably having from 2 to 10 carbon atoms per molecule. Typical species include cobalt or nickel octoate, iron hexoate and the like. The catalyst components may be added directly to the unsaturated compound or may be blended and added as a dispersion or solution to the organic unsaturated compound. Hydrogenation is continued at temperatures from about room temperature to about 200°C, usually between about 25° and 150°C, still more preferably between about 35° and 125°C. Hydrogenation time will depend in part upon the temperature and hydrogen pressure and in part upon the reactivity of the unsaturated compound. Normally, hydrogenation will be carried out for periods between about 5 minutes and 8 hours, usually for a time between about 30 minutes and 4 hours. Preferably, the unsaturated compound (with particular reference to the polymeric compounds) is conducted in a relatively inert solvent such as aliphatic or naphthenic hydrocarbon or mixtures thereof. Hydrogenation pressures are usually below about 5,000 psi, usually in the order to 250–1500 psi. The weight ratio of cobalt, nickel or iron to unsaturated compound will vary between wide limits but normally is between about $10^{-5}$ and about $10^{-2}$.

After the hydrogenation has been carried to an extent believed sufficient to warrant either analysis of the product or interruption of the hydrogenation, the process of the present invention comes into play whereby a supplementary amount of the same or different organometallic reducing agent is injected into the hydrogenation reaction mixture. Preferably, this supplementary amount is in the order of 0.75 to 2.5 moles per mole of cobalt, nickel or iron compound used in the preparation of the original catalyst. Injection may be by addition of the supplementary agent in the form of a solution in an inert solvent. Alternatively, the injection may be by means of feeding the supplementary material into a slip stream and recycling back to the hydrogenation vessel.

Another important reason for interrupting hydrogenation is concerned with plant schedules. In the normal course of plant operation, it may be necessary to hold the hydrogenation reaction mixture for a period of time before further working up due to the fact that the subsequent pieces of plant equipment such as vats, coagulators or the like may already be temporarily occupied with previous batches. Consequently, it is advisable to interrupt the hydrogenation during such holding periods so that the product is not hydrogenated beyond the desired extent.

The injection of the supplementary agent effectively interrupts hydrogenation and hence permits the withdrawal of samples for analysis, the addition of other process components, the holding of the reaction mixture without hydrogenation or for any other desired objective. The hydrocarbyl groups are preferably alkyl, aromatic or naphthenic hydrocarbons, preferably having from 2 to 10 carbon atoms each.

Subsequent to the interruption step, the reaction product may be treated either to permit resumption of hydrogenation or recovery of the hydrogenated product if this is indicated by analysis of samples withdrawn therefrom. The interrupting effect of the aluminum trihydrocarbyl is reversed by reaction of the supplementary amount with an aliphatic alcohol, polyhydric alcohol, carboxylic acid or water or with a supplementary carboxylate or alkoxide of cobalt, nickel or aluminum. The use of an alcohol is preferred. Although water is the lowest cost reactant for this purpose, its low solubility in hydrocarbons is unfavorable. Preferred alcohols are aliphatic monohydric alcohols having from 1 to 14 carbon atoms, including especially alcohols from methyl to octyl. The amount of these reactants injected will be sufficient to react with the reducing agent at least to the extent that interruption of hydrogenation is effectively eliminated and hydrogenation can be resumed. Most reactants require a molar equivalence, i.e. approximately a mole of reactant for each mole of aluminum trihydrocarbyl added for interruption.

The conditions of resumed hydrogenation may be the same or may be different from those utilized prior to interruption. For example, if a copolymer of a conjugated diene and alkenylarene is being hydrogenated and analysis of the product during the interruption period indicates that all of the aliphatic unsaturation has been reduced, then hydrogenation conditions such as temperature may be increased to a point that hydrogenation of the unsaturation in the alkenylarene units takes place if this is desired. It is possible, of course, to utilize more than one interruption stage if this is necessary for periodic analysis or holding periods. The following examples illustrate the process of the present invention.

EXAMPLE I

A copolymer of styrene and isoprene was prepared by polymerization of a mixture of the two monomers in cyclohexane solution, resulting in a tapered copolymer having 37.5 wt.% styrene. The polymer, in cyclohexane solvent, was then subjected to hydrogenation utilizng a catalyst comprising the reaction product of 2.5 moles of aluminum triethyl per mole of nickel-2-ethylhexoate. The hydrogenation reacton conditions comprised 700 psig hydrogen pressure, 80°C, 18% polymer solids in the solution and 4.0 mmoles nickel per pound of polymer. After 180 minutes hydrogenation time, 93.5% of the olefinic unsaturation had been reduced. At this point, triethyl aluminum (TEA) was added, causing substantially complete interruption of hydrogenation. This was indicated by the fact that after holding for 30 additional minutes, the percent of hydrogenation of olefinic bonds had only increased about 1%. In a parallel run with no supplemental TEA being added, the percentage of olefin reduction is about 97.3% after a total of 210 minutes hydrogenation under the same conditions. In the process according to the invention as described above, one mole of supplemental TEA was added per mole of nickel.

EXAMPLE II

Essentially the same conditions were utilized for the hydrogenation of the same type of polymer. Parallel runs were made in one of which, according to the process of the invention, supplemental TEA was added at about 94.5% olefin bond reduction in the polymer.

According to FIG. I, it will be seen that this substantially completely interrupted hydrogenation as indicated by analysis for olefins in three successive time periods following the point of TEA addition.

In a parallel experiment, interruption of hydrogenation was attempted by depressing from 700 to 100 psig hydrogen pressure and reducing the rate of stirring from 920 rpm to 200 rpm. The course of hydrogenation is indicated by curve B on FIG. I. It will be noted that depressuring and reduction in stirring speed caused a moderate decrease in the rate of hydrogenation, but that hydrogenation continued in spite of these changes in reaction conditions. This indicates that a given target of residual olefin content could not be desirably achieved by these two changes in reaction conditions, but, as shown by curve A (process according to the invention) close control of target residual olefin is readily achieved by the addition of TEA without reducing hydrogen pressure or stirring speed.

EXAMPLE III

Restoration of hydrogenation activity to an interrupted hydrogenation reaction mixture can be achieved as shown below wherein supplemental 2-ethylhexanol was injected into the mixture which had been interrupted by the addition of supplemental TEA. In this case, the original catalyst comprised the reaction product of three moles of TEA per mole of nickel-2-ethylhexoate, 11.1 mmoles nickel per pound of polymer being utilized. Hydrogenation of the polymer was continued at 700 psig hydrogen pressure at 90°C. The solution contained 16.2 wt.% of the polymer which was a block copolymer having the structure polystyrene-polyisoprene in which the block molecular weights were 30,000 and 50,000. Hydrogenation was continued initially intil 25% of the olefinic unsaturation in the block copolymer had disappeared. At this point 22.2 mmoles of supplemental TEA per pound of polymer was added to the reaction mixture causing virtually complete interruption of hydrogenation. 2-Ethylhexanol was then added incrementally to the reaction mixture to determine the effect of its addition at various ratios relative to the supplemental TEA. The table below shows that the hydrogenation was resumed and that the rest of hydrogenation was readily controllable by deliberate limitation of the amount of TEA eliminated by reaction with the 2-ethylhexanol.

Table I

| EFFECT OF EXCESS TEA ON CATALYST ACTIVITY | | |
|---|---|---|
| 2-ethylhexanol ml | Added alcohol mmole/lb. polymer | Olefin Loss ($t_{1/2}$ (min))[1] |
| 0 | 0 | ∞ |
| 5 | 5.86 | 330 |
| 6 | 7.02 | 230 |
| 7 | 8.19 | 150 |
| 8 | 9.36 | 93 |

Table I-continued

| EFFECT OF EXCESS TEA ON CATALYST ACTIVITY | | |
|---|---|---|
| 2-ethylhexanol ml | Added alcohol mmole/lb. polymer | Olefin Loss ($t_{1/2}$ (min))[1] |
| 9 | 10.52 | 75 |
| 10 | 11.70 | 53 |
| 12 | 14.04 | 43 |
| 14 | 16.38 | 32 |
| Blank Experiment with no excess TEA | | |
| — | — | 22 |

[1] Time in minutes for half of the starting olefin content of the polymer to disappear.

What is claimed is:

1. In the process for the hydrogenation of polymers of olefinically unsaturated hydrocarbons wherein the hydrocarbons are hydrogenated in the presence of a catalyst comprising the reaction product of 1.0–5.0 moles of an aluminum trihydrocarbyl per mole of an alkoxide or carboxylate of a metal of the group consisting of cobalt, nickel, iron or mixtures thereof, the improvement comprising hydrogenating the hydrocarbon and thereafter reversibly interrupting the hydrogenation by injection of supplementary aluminum trihydrocarbyl in an amount between 0.75 and 2.5 moles per mole of cobalt, nickel or iron.

2. A process according to claim 1 wherein the hydrogenation catalyst is the reaction product of an aluminum trihydrocarbyl and a carboxylate of cobalt, iron or nickel and hydrogenation is reactivated subsequent to interruption by injecton of at least one carboxylate of cobalt, nickel or iron in an amount between about 0.4 and 1.5 moles per mole of supplementary aluminum trihydrocarbyl.

3. A process according to claim 1 wherein hydrogenation is reactivated subsequent to interruption by injection of an aliphatic monohydric alcohol that is soluble in the reaction medium in an amount between 0.75 and 2.5 moles per mole of supplementary aluminum trihydrocarbyl.

4. A process according to claim 1 wherein the polymer comprises a polymerized conjugated diene.

5. A process according to claim 4 wherein the polymer comprises a copolymer of at least one monoalkenylarene and at least one conjugated diene.

6. A process according to claim 5 wherein the copolymer is a block copolymer.

7. A process according to claim 3 wherein the alcohol is an aliphatic alcohol having 2–14 carbon atoms per molecule.

8. A process according to claim 4 wherein hydrogenation is interrupted after at least about 90% of the olefinic double bonds have been reduced by hydrogenation.

9. A process according to claim 6 wherein the polymer is a block copolymer having the structure polystyrene-polyisoprene.

10. A process according to claim 6 wherein the polymer is a block copolymer having the structure polystyrene-polybutadiene-polystyrene.

* * * * *